United States Patent [19]

McRae

[11] Plant 4,177

[45] Jan. 3, 1978

[54] LILY PLANT: LILIUM 'SHOWBOAT'

[75] Inventor: Edward A. McRae, Boring, Oreg.

[73] Assignee: Melridge, Inc., Gresham, Oreg.

[21] Appl. No.: 761,228

[22] Filed: Jan. 21, 1977

[51] Int. Cl.[2] ..... A01H 5/00

[52] U.S. Cl. ..... Plt./68

[58] Field of Search ..... Plt./68

*Primary Examiner*—Robert E. Bagwill

*Attorney, Agent, or Firm*—Eugene D. Farley

[57] ABSTRACT

A new variety of Asiatic hybrid lily plant bearing large clusters of medium-sized flowers of excellent form, strong color, and long persistence, both on the plant and as a cut flower; the flowers of the new plant being particularly characterized by their deep blood red color which is unique in the division of hybrid lilies to which the plant belongs. The plant is a good propagator, highly resistant to disease, and tolerant to virus. It is a good grower and excellent when precooled bulbs are forced out of season.

1 Drawing Figure

BACKGROUND OF THE INVENTION

My new variety of lily plant originated as a seedling selected from a group of seedlings at Gresham, Oreg. The seedlings were planted as a part of a breeding program carried on by me since the year 1965. This program had as its objective the production of upright Asiatic lilies having an intense red color, heretofore unknown in this division of hybrid lilies.

I achieved the desired objective by using as a seed parent Lilium X 'Sunspot' and as the pollen parent Lilium X 'Byam's Ruby'.

This new lily plant is characterized by a flower of the deepest, most intense blood red color in the division of genus Lilium to which it belongs. In this respect it is vastly superior to such lily varieties as Lilium 'Tabasco' and Lilium 'Cinnabar'. Its color is one of the most intense yet seen in non-pendant lilies, and, unlike most scarlet lilies, its appearance is not altered by artificial light. The flowers are large, having a diameter of about 6 inches and grow in clusters of numerous blooms. They hold their color until the tepals drop.

In addition, the plant is a good propagator, highly resistant to disease and tolerant to virus infection. It possesses all of the desired characteristics of excellence of form, color and habit. The clone is vigorous and a good grower and propagator, as observed at Gresham, Oreg.

My new variety of lily plant has been asexually reproduced by me and under my direction at Gresham, Oreg. Successive generations produced by bulb scale reproduction and natural propagation from bulblets have demonstrated that the novel and distinctive characteristics of my new variety are fixed and hold true from generation to generation.

DESCRIPTION OF THE DRAWING

My new variety of lily plant is illustrated in the accompanying photographic drawing which shows the open bloom in full color and illustrates the flower form, the tepal arrangement, the connection of the flowers to the stalk and in particular the novel and distinctive intense blood red color tone of the flower.

DESCRIPTION OF THE NEW VARIETY

The following is a detailed description of my new variety of Asiatic hybrid lily, with nomenclature according to *The International Lily Register* (Royal Horticultural Society, London, 2nd edition, 1969), and with color designations according to the Royal Horticultural Society Color Chart, published by the Royal Horticultural Society in 1966.

THE PLANT

Origin: Seedling.

Parentage:

- *Seed parent.*—Lilium X 'Sunspot' clone (unpatented).
- *Pollen parent.*—Lilium X 'Byam's Ruby' (unpatented).

Classification:

- *Botanic.*—Lilium hybrid clone; Division I-A of classification Lilium.
- *Commercial.*—Asiatic hybrid lily.

Form: Single stem, erect and stately.

Height: 20 to 25 inches.

Growth: Vigorous and upright.

Foliage:

- *Quantity.*—Abundant.
- *Size of leaf.*—3 to 4 inches long.
- *Shape of leaf.*—Lanceolate.
- *Texture.*—Glossy.
- *Color.*—Upper and undersides both dark green with reddish infusion.

Bulbs:

- *Size.*—Any size ranging up to 10 inches in circumference.
- *Color.*—Reddish, especially upon exposure to light.

THE BUD

Form: Obtuse, urn-shaped and long.

Size: 2 to 3 inches long and 1½ inches in circumference at maturity.

Opening: Bud opens slowly.

Color: Deep blood red when tepals first divide and also when tepals begin to unfurl.

Tepals: Deep blood red both inside and outside.

Peduncle: 2 inches long; slightly hairy; erect; deep green in color.

THE FLOWER

Blooming habit: Recurrent, Blooms once and profusely, annually in mid season.

Size: Medium; about 6 inches in diameter.

Borne: In clusters, from 6 to 12 on a single stem.
Shape: Cup shaped when bloom first opens; flower reflexes to almost flat shape as it ages.
Tepalage:
*Number of tepals.*—6.
*Arrangement.*—Imbricated.
*Color.*—Deepest blood red R.H.S. C.C.46A-B substantially entirely across the tepal surfaces; white pubescence along margins of nectaries.
*Tepal longevity.*—Tepals stay on stem about 3 weeks.
Pedicel:
*Length.*—2 inches.
*Color.*—Deepest green with reddish tinge.
*Form.*—Pedicel is sturdy and upright.
Color permanence: Flowers hold color until tepals drop.
Appearance: The flower is shiny.
Disease resistance: The plant and flower are resistant to disease; in particular, they are resistant to Fusarium and Botrytis.
Fragrance: The flower is not fragrant.
Lasting quality: The flower is long lasting both on the plant and as a cut flower.

THE REPRODUCTIVE ORGANS

Stamens, anthers:

*Arrangement.*—Typical of Liliaceae.
*Length.*—2 inches.
*Number.*—6.
*Filaments.*—Length, 2 inches; color, cream.
Pollen and anthers: Dark reddish-brown in color.
Pistils: One in number with a length of about 2 inches.
Stigma: Dark red in color.
Characteristics of ovaries: Typical of genus Lilium.

FRUIT

Fertility: The fruit is fertile.
Shape: The fruit is ovoid in shape.
Color at maturity: The fruit is soft brown at maturity.

My new variety of Asiatic hybrid lily is unique. It does not resemble any other lily in its class.

I claim:

1. A new and distinctive variety of Asiatic hybrid lily plant substantially as herein shown and described, characterized by its high resistance to disease, its tolerance to virus, the vigorous growth and propagation characteristics of its clone; its versatility both as a garden plant and a plant produced from precooled bulbs forced for cut flower and pot plant; its erect and stately form; the excellence of its flower form; and particularly by the intense blood red color of its flowers.

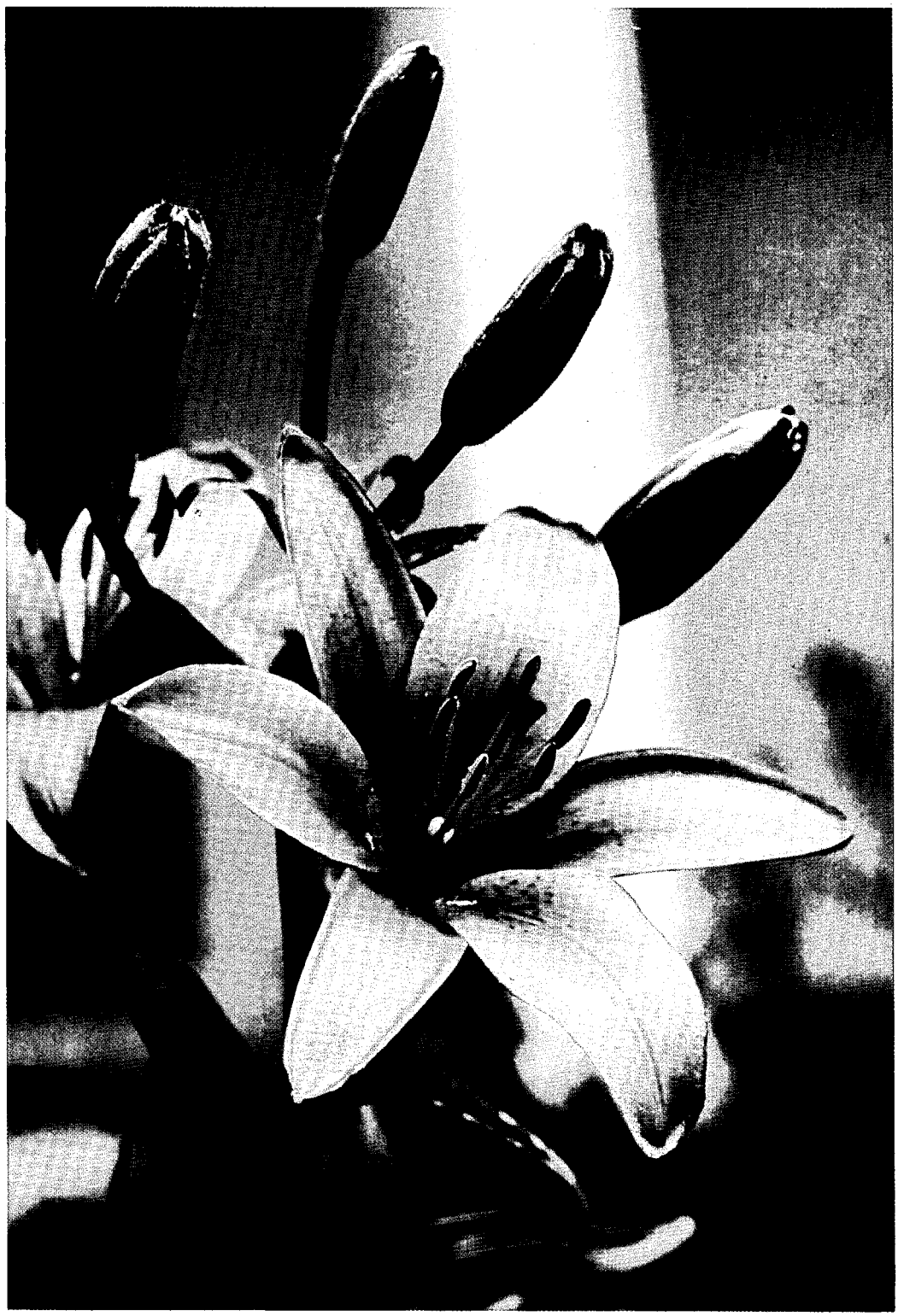

* * * * *